US012582463B2

(12) United States Patent
Daly et al.

(10) Patent No.: US 12,582,463 B2
(45) Date of Patent: Mar. 24, 2026

(54) ABLATION CATHETER TIP WITH FLEXIBLE ELECTRONIC CIRCUITRY

(71) Applicant: St. Jude Medical International Holding S.à r.l., Luxembourg (LU)

(72) Inventors: Jacob J. Daly, Ham Lake, MN (US); Brett A. Hillukka, Hanover, MN (US)

(73) Assignee: St. Jude Medical International Holding S.à r.l., Luxembourg (LU)

( * ) Notice: Subject to any disclaimer, the term of this patent is extended or adjusted under 35 U.S.C. 154(b) by 241 days.

(21) Appl. No.: 16/844,571

(22) Filed: Apr. 9, 2020

(65) Prior Publication Data

US 2020/0323585 A1 Oct. 15, 2020

Related U.S. Application Data

(60) Provisional application No. 62/832,248, filed on Apr. 10, 2019.

(51) Int. Cl.
| | |
|---|---|
| *A61B 18/14* | (2006.01) |
| *A61B 5/00* | (2006.01) |
| *A61B 5/287* | (2021.01) |
| *A61B 18/00* | (2006.01) |

(52) U.S. Cl.
CPC .......... *A61B 18/1492* (2013.01); *A61B 5/287* (2021.01); *A61B 5/6852* (2013.01); *A61B 2018/00077* (2013.01); *A61B 2018/00101* (2013.01); *A61B 2018/00351* (2013.01); *A61B 2018/00577* (2013.01); *A61B 2018/00642* (2013.01); *A61B 2018/00797* (2013.01); *A61B*

*2018/00821* (2013.01); *A61B 2018/00839* (2013.01); *A61B 2218/002* (2013.01); *A61B 2562/028* (2013.01)

(58) Field of Classification Search
CPC .............. A61B 18/1492; A61B 5/6852; A61B 2018/00077; A61B 2018/00101; A61B 2018/00577; A61B 2018/00797; A61B 2018/00821; A61B 2018/00839; A61B 2218/002

See application file for complete search history.

(56) References Cited

U.S. PATENT DOCUMENTS

| | | | |
|---|---|---|---|
| 8,567,265 B2 | 10/2013 | Leo et al. | |
| 11,026,745 B2 * | 6/2021 | Guler ................... | A61B 5/6852 |
| 2010/0063478 A1 | 3/2010 | Selkee | |
| 2011/0224667 A1 * | 9/2011 | Koblish ............. | A61B 18/1492 |
| | | | 606/41 |
| 2014/0171936 A1 * | 6/2014 | Govari ............... | A61B 18/1492 |
| | | | 606/34 |

(Continued)

FOREIGN PATENT DOCUMENTS

WO 2019175706 A1 9/2019

*Primary Examiner* — Thomas A Giuliani
*Assistant Examiner* — Abigail M Ziegler
(74) *Attorney, Agent, or Firm* — DENTONS Durham Jones Pinegar

(57) ABSTRACT

Aspects of the present disclosure are directed to, for example, a high-thermal-sensitivity ablation catheter tip with force measurement capability. More specifically, various aspects of the present disclosure are directed to improving the deformation consistency of the ablation catheter tip in response to various forces, and thereby improving force measurement accuracy of an ablation catheter system.

14 Claims, 5 Drawing Sheets

(56)  References Cited

U.S. PATENT DOCUMENTS

| | | | |
|---|---|---|---|
| 2014/0276759 A1* | 9/2014 | Kim | A61B 18/1492 |
| | | | 606/33 |
| 2014/0276788 A1* | 9/2014 | Nguyen | A61B 18/1492 |
| | | | 606/41 |
| 2016/0045133 A1 | 2/2016 | Balachandran et al. | |
| 2016/0143690 A1* | 5/2016 | Schultz | A61B 5/01 |
| | | | 606/41 |
| 2016/0183821 A1* | 6/2016 | Pai | A61B 5/283 |
| | | | 604/21 |
| 2016/0192982 A1 | 7/2016 | Tegg et al. | |
| 2016/0287312 A1 | 10/2016 | Tegg et al. | |
| 2016/0287326 A1 | 10/2016 | Tegg et al. | |
| 2016/0331471 A1 | 11/2016 | Deno et al. | |
| 2017/0042449 A1 | 2/2017 | Balachandran et al. | |
| 2017/0049348 A1 | 2/2017 | Balachandran et al. | |
| 2018/0000542 A1* | 1/2018 | Oliverius | A61B 18/1492 |
| 2018/0071017 A1* | 3/2018 | Bar-Tal | A61B 18/1492 |
| 2018/0092688 A1 | 4/2018 | Tegg | |
| 2018/0092689 A1 | 4/2018 | Hillukka et al. | |
| 2018/0296111 A1 | 10/2018 | Deno et al. | |
| 2018/0353238 A1* | 12/2018 | Schultz | A61B 18/1492 |
| 2019/0038228 A1 | 2/2019 | Daly | |
| 2020/0030024 A1* | 1/2020 | Rao | A61B 18/1492 |
| 2020/0038100 A1 | 2/2020 | Hillukka et al. | |
| 2020/0093396 A1 | 3/2020 | Romoscanu | |

* cited by examiner

ABLATION CATHETER TIP WITH FLEXIBLE ELECTRONIC CIRCUITRY

CROSS-REFERENCE TO RELATED APPLICATIONS

This application claims the benefit of U.S. provisional application No. 62/832,248, filed 10 Apr. 2019, which is hereby incorporated by reference as though fully set forth herein.

This application incorporates by reference as though fully set forth herein: U.S. application Ser. No. 15/088,036, filed 31 Mar. 2016, which claims the benefit of U.S. provisional application No. 62/141,066, filed 31 Mar. 2015; U.S. application Ser. No. 15/088,052, filed 31 Mar. 2016, which claims the benefit of U.S. provisional application No. 62/198,114, filed 28 Jul. 2015; U.S. application Ser. No. 15/723,701, filed 3 Oct. 2017, which claims the benefit of U.S. provisional application No. 62/404,038, filed 4 Oct. 2016; U.S. application Ser. No. 15/724,157, filed 3 Oct. 2017, which claims the benefit of U.S. provisional application No. 62/404,060, filed 4 Oct. 2016; international application no. PCT/US2017/049264, filed 30 Aug. 2017, which claims the benefit of U.S. provisional application No. 62/404,013, filed 4 Oct. 2016; U.S. provisional application No. 62/642,178, filed 13 Mar. 2018 U.S. provisional application No. 62/824,840, filed 27 Mar. 2019; U.S. provisional application No. 62/824,844, filed 27 Mar. 2019; and U.S. provisional application No. 62/824,846, filed 27 Mar. 2019.

BACKGROUND OF THE DISCLOSURE a. Field

The instant disclosure relates to various types of medical catheters, in particular catheters for diagnostics within, and/or treatment of, a patient's cardiovascular system. In one embodiment, the instant disclosure relates to an ablation catheter for treating cardiac arrhythmias within a cardiac muscle. Various aspects of the instant disclosure relate to force sensing systems capable of determining a force applied at a distal tip of the ablation catheter.

The present disclosure further relates to low thermal mass ablation catheter tips (also known as high-thermal-sensitivity catheter tips) and to systems for controlling the delivery of RF energy to such catheters during ablation procedures.

b. Background

Exploration and treatment of various organs or vessels has been made possible using catheter-based diagnostic and treatment systems. These catheters may be introduced through a vessel leading to the cavity of the organ to be explored, and/or treated. Alternatively, the catheter may be introduced directly through an incision made in the wall of the organ. In this manner, the patient avoids the trauma and extended recuperation times typically associated with open surgical procedures.

The human heart routinely experiences electrical currents traversing its many layers of tissue. Just prior to each heart contraction, the heart depolarizes and repolarizes as electrical currents spread across the heart. In healthy hearts, the heart will experience an orderly progression of depolarization waves. In unhealthy hearts, such as those experiencing atrial arrhythmia, including for example, ectopic atrial tachycardia, atrial fibrillation, and atrial flutter, the progression of the depolarization wave becomes chaotic.

Catheters are used in a variety of diagnostic and/or therapeutic medical procedures to diagnose and correct conditions such as atrial arrhythmia. Typically, in such a procedure, a catheter is manipulated through a patient's vasculature to the patient's heart carrying one or more end effectors which may be used for mapping, ablation, diagnosis, or other treatment. Where an ablation therapy is desired to alleviate symptoms including atrial arrhythmia, an ablation catheter imparts ablative energy to cardiac tissue to create a lesion in the cardiac tissue. The lesioned tissue is less capable of conducting electrical signals, thereby disrupting undesirable electrical pathways and limiting or preventing stray electrical signals that lead to arrhythmias. The ablation catheter may utilize ablative energy including, for example, radio frequency (RF), cryoablation, laser, chemical, and high-intensity focused ultrasound. Ablation therapies often require precise positioning of the ablation catheter, as well as precise pressure exertion for optimal ablative-energy transfer into the targeted myocardial tissue. Excess pressure between the ablation catheter tip and the targeted myocardial tissue may result in excessive ablation which may permanently damage the cardiac muscle and/or surrounding nerves. When the contact pressure between the ablation catheter tip and the targeted myocardial tissue is below a target pressure, the efficacy of the ablation therapy may be reduced.

Ablation therapies are often delivered by multiple applications of ablation energy at points in close proximity in a controlled fashion in order to form a lesion line. To improve conformity of the individual ablations along the lesion line, it is desirable to precisely control the position at which the individual ablation energy is delivered, the ablation period, and the contact pressure between the ablation catheter tip and the targeted tissue. All of these factors affect the conformity of the resulting lesion line.

The foregoing discussion is intended only to illustrate the present field and should not be taken as a disavowal of claim scope.

BRIEF SUMMARY OF THE DISCLOSURE

It is desirable to control the delivery of RF energy to a catheter to enable the creation of lesions in tissue, by keeping the generator power setting sufficiently high to form adequate lesions, while mitigating against overheating of tissue. Accordingly, aspects of the present disclosure are directed toward an ablation catheter tip including high thermal sensitivity materials which facilitate near real-time temperature sensing at the ablation catheter tip. Further aspects of the present disclosure are directed to improved ablation catheter force measurements in response to tissue contact on the ablation catheter tip.

One embodiment of the present disclosure is directed to an ablation catheter tip. The ablation catheter tip including a conductive shell, structural member, and a manifold. The conductive shell includes a dispersion chamber for irrigant distribution. The structural member is coupled to a proximal end of the conductive shell, and deflects in response to a force exerted on the conductive shell. The manifold includes an irrigation lumen extending through a longitudinal axis of the manifold. The irrigation lumen delivers irrigant into the dispersion chamber. The manifold further includes a distal portion that is welded to a distal portion of the structural member. In further more specific embodiments, the distal portion of the structural member is welded to a proximal portion of the conductive shell.

In another embodiment of the present disclosure a method for assembling an ablation catheter tip is disclosed. The method includes providing a manifold with an irrigant lumen extending there through, providing a structural member with an annulus, inserting the manifold into the annulus of the structural member, and welding a distal portion of the structural member to a distal portion of the manifold. In more specific embodiments, the method further includes providing a conductive shell, and welding a proximal portion of the conductive shell to the distal portion of the structural member.

The foregoing and other aspects, features, details, utilities, and advantages of the present disclosure will be apparent from reading the following description and claims, and from reviewing the accompanying drawings.

DESCRIPTION OF THE DRAWINGS

Various example embodiments may be more completely understood in consideration of the following detailed description in connection with the accompanying drawings.

Figure 1:
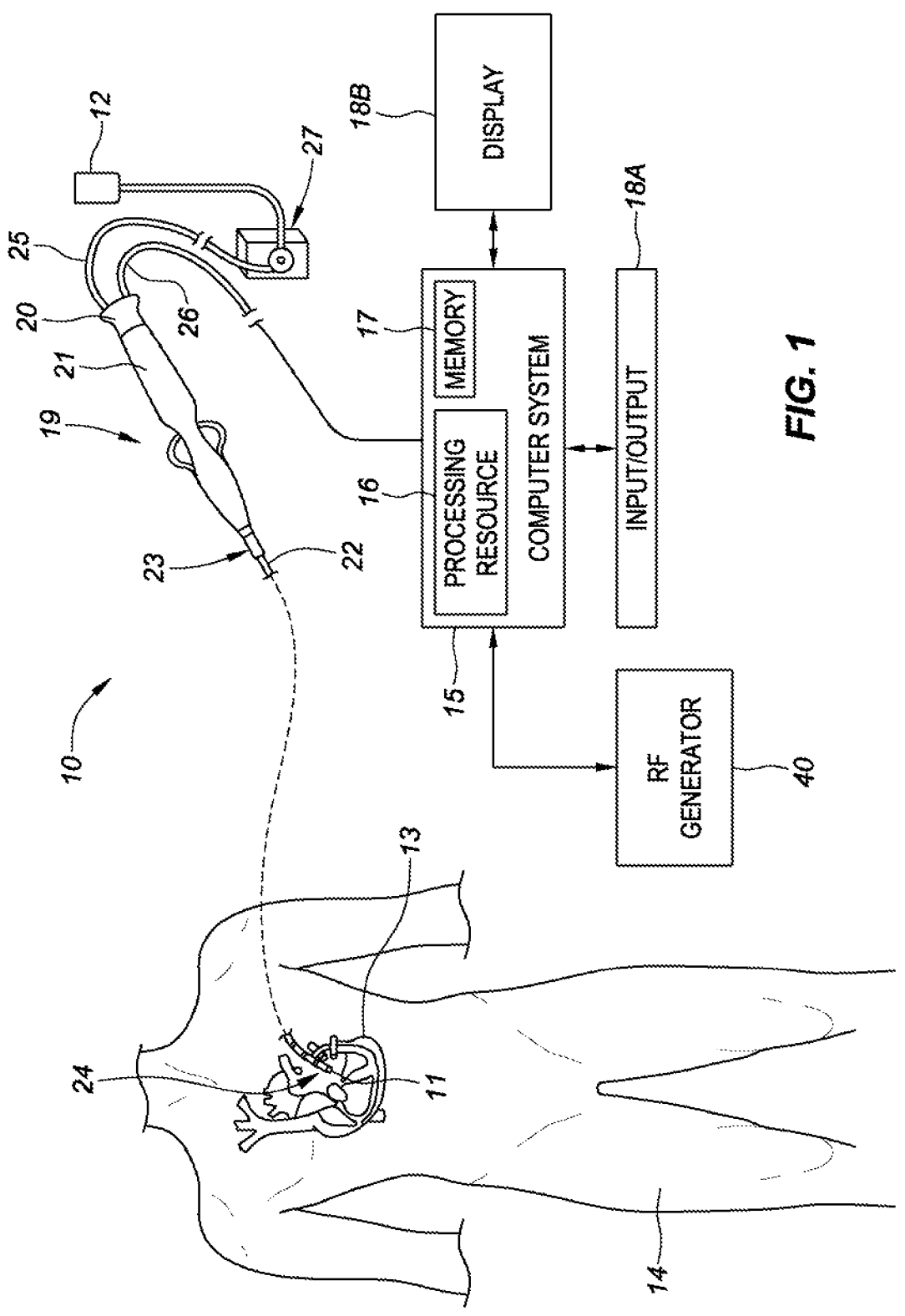
FIG. 1 is a diagrammatic overview of an ablation catheter system including a force sensing subsystem, consistent with various embodiments of the present disclosure.

While various embodiments discussed herein are amenable to modifications and alternative forms, aspects thereof have been shown by way of example in the drawings and will be described in detail. It should be understood, however, that the intention is not to limit the invention to the particular embodiments described. On the contrary, the intention is to cover all modifications, equivalents, and alternatives falling within the scope of the disclosure including aspects defined in the claims. In addition, the term "example" as used throughout this application is only by way of illustration, and not limitation.

DETAILED DESCRIPTION OF EMBODIMENTS

In a typical ablation therapy for atrial fibrillation, pulmonary veins are treated. A distal tip of a catheter may include electrodes (also referred to as spot electrodes) which help to expedite diagnosis and treatment of a source of a cardiac arrhythmia, and may also be used to confirm a successful ablation therapy by determining the isolation of arrhythmic foci within one or more of the pulmonary veins from the left atrium, for example, or the destruction of the arrhythmic foci entirely.

During an ablation therapy, a distal end of an ablation catheter tip contacts ablation targeted myocardial tissue in order to conductively transfer energy (e.g., radio-frequency, thermal, etc.) thereto. It has been discovered that consistent force, during a series of tissue ablations, forms a more uniform and transmural lesion line. Such uniform lesion lines have been found to better isolate the electrical impulses produced by arrhythmic foci, thereby improving the overall efficacy of the ablation therapy. To achieve such consistent force, aspects of the present disclosure utilize a deformable body in the ablation catheter tip. The deformable body deforms in response to forces being exerted upon a distal end of the ablation catheter tip. The deformation of the deformable body may then be measured by a measurement device (e.g., ultrasonic, magnetic, optical, interferometry, etc.). Based on the tuning of the deformable body and/or the calibration of the measurement device, the deformation may then be associated with a force exerted on the distal end of the ablation catheter tip (e.g., via a lookup table, formula(s), calibration matrix, etc.).

Various other aspects of the present disclosure are directed to high thermal sensitivity monitoring of an ablation tip of the catheter, the sensed temperature indicative of the targeted tissue temperature during an ablation therapy. The combination of force sensing and high-thermal sensitivity monitoring facilitate improved patient outcomes.

Referring now to the drawings wherein like reference numerals are used to identify identical components in the various views, FIG. 1 generally illustrates an ablation catheter system 10 having an elongated medical device 19 that includes a sensor assembly 11 (e.g., fiber optic based distance measurement sensor) configured to be used in the body for medical procedures. The elongated medical device 19 may be used for diagnosis, visualization, and/or treatment of tissue 13 (such as cardiac or other tissue) in a patient's body 14. For example, the medical device 19 may be used for ablation therapy of tissue 13 or mapping of a patient's body 14. FIG. 1 further illustrates various sub-systems included in the ablation catheter system 10. The system 10 may include a main computer system 15 (including an electronic control unit 16 (also referred to as a "processing resource") and data storage 17, e.g., memory). The computer system 15 may further include conventional interface components, such as various user input/output mechanisms 18A and a display 18B, among other components. Information provided by the sensor assembly 11 may be processed by the computer system 15 and may provide data to the clinician via the input/output mechanisms 18A and/or the display 18B, or in other ways as described herein. Specifically, the display 18B may visually communicate a force exerted on the elongated medical device 19—where the force exerted on the elongated medical device 19 is detected in the form of a deformation of at least a portion of the elongated medical device by the sensor assembly 11, and the measured deformation is processed by the computer system 15 to determine the force exerted.

In the illustrative embodiment of FIG. 1, the elongated medical device 19 may include a cable connector or interface 20, a handle 21, a tubular body or shaft 22 having a proximal end 23 and a distal end 24. The elongated medical device 19 may also include other conventional components not illustrated herein, such as a temperature sensor, additional electrodes, and corresponding conductors or leads. The connector 20 may provide mechanical, fluid and/or electrical connections for cables 25, 26 extending from a fluid reservoir 12 and a pump 27 and the computer system 15, respectively. The connector 20 may comprise conventional components known in the art and, as shown, may be disposed at the proximal end of the elongated medical device 19.

The handle 21 provides a portion for a user to grasp or hold the elongated medical device 19 and may further provide a mechanism for steering or guiding the shaft 22 within the patient's body 14. For example, the handle 21 may include a mechanism configured to change the tension on a pull-wire extending through the elongated medical device 19 to the distal end 24 of the shaft 22 or some other mechanism to steer the shaft 22. The handle 21 may be conventional in the art, and it will be understood that the configuration of the handle 21 may vary. In an embodiment, the handle 21 may be configured to provide visual, auditory, tactile and/or other feedback to a user based on information received from the sensor assembly 11. For example, if contact to tissue 13 is made by distal end 24, the sensor assembly 11 may transmit data to the computer system 15 indicative of contact. In response to the computer system 15 determining that the data received from the sensor assembly 11 is indicative of contact between the distal end 24 and a patient's body 14, the computer system 15 may operate a light-emitting-diode on the handle 21, a tone generator, a vibrating mechanical transducer, and/or other indicator(s), the outputs of which could vary in proportion to the calculated contact force.

The computer system 15 may utilize software, hardware, firmware, and/or logic to perform a number of functions described herein. The computer system 15 may be a combination of hardware and instructions to share information. The hardware, for example may include processing resource 16 and/or a memory 17 (e.g., non-transitory computer-readable medium (CRM) database, etc.). A processing resource 16, as used herein, may include a number of processors capable of executing instructions stored by the memory resource 17. Processing resource 16 may be integrated in a single device or distributed across multiple devices. The instructions (e.g., computer-readable instructions (CRI)) may include instructions stored on the memory 17 and executable by the processing resource 16 for force detection.

The memory resource 17 is communicatively coupled with the processing resource 16. A memory 17, as used herein, may include a number of memory components capable of storing instructions that are executed by processing resource 16. Such a memory 17 may be a non-transitory computer readable storage medium, for example. The memory 17 may be integrated in a single device or distributed across multiple devices. Further, the memory 17 may be fully or partially integrated in the same device as the processing resource 16 or it may be separate but accessible to that device and the processing resource 16. Thus, it is noted that the computer system 15 may be implemented on a user device and/or a collection of user devices, on a mobile device and/or a collection of mobile devices, and/or on a combination of the user devices and the mobile devices.

The memory 17 may be communicatively coupled with the processing resource 16 via a communication link (e.g., path). The communication link may be local or remote to a computing device associated with the processing resource 16. Examples of a local communication link may include an electronic bus internal to a computing device where the memory 17 is one of a volatile, non-volatile, fixed, and/or removable storage medium in communication with the processing resource 16 via the electronic bus.

In various embodiments of the present disclosure, the computer system 15 may receive optical signals from a sensor assembly 11 via one or more optical fibers extending a length of the catheter shaft 22. A processing resource 16 of the computer system 15 may execute an algorithm stored in memory 17 to compute a force exerted on distal end 24, based on the received optical signals.

U.S. Pat. No. 8,567,265 discloses various optical force sensors for use in medical catheter applications, such optical force sensors are hereby incorporated by reference as though fully disclosed herein.

FIG. 1 further depicts an RF generator 40 operatively connected to the computer system 15, which is operatively connected to the elongated medical device 19. In this figure, a number of possible wired and/or wireless communication pathways are shown. For example, the computer system 15 may receive temperature feedback readings from at least one temperature sensor mounted on or near the distal end 24 of the catheter shaft 22. In various embodiments disclosed herein, the catheter may include multiple thermal sensors (for example, thermocouples or thermistors), as described further below. The temperature feedback readings may be the highest reading from among all of the individual temperature sensor readings, or it may be, for example, an average of all of the individual readings from all of the temperature sensors. The computer system 15 may then communicate to the RF generator 40 the highest temperature measured by any of the plurality of temperature sensors mounted within the sensor assembly 11. This could be used to trigger a temperature-based shutdown feature in the RF generator for patient safety. In other words, the temperature reading or readings from the catheter may be sent to the computer system 15, which may then feed the highest temperature reading to the RF generator 40 so that the generator can engage its safety features and shut down (or titrate power) if the temperature reading exceeds a (safety) threshold.

In an alternative operation of the system 10 of FIG. 1, the computer system 15, in response to elevated temperature feedback from the thermal sensors, may operate the RF generator 40 in a pulsed manner. By pulsing the RF signal, the power may remain at a desired power level (e.g., 50 or 60 Watts) rather than being reduced to an ineffective level when excessive temperature is sensed by the catheter tip. By pulsing the power to control temperature, for example controlling the length of pulse and gaps between pulses, tip temperature may be controlled.

In the embodiment depicted in FIG. 1, the RF generator 40 may include pulse control hardware, software, and/or firmware built into the generator itself.

Figure 2A:
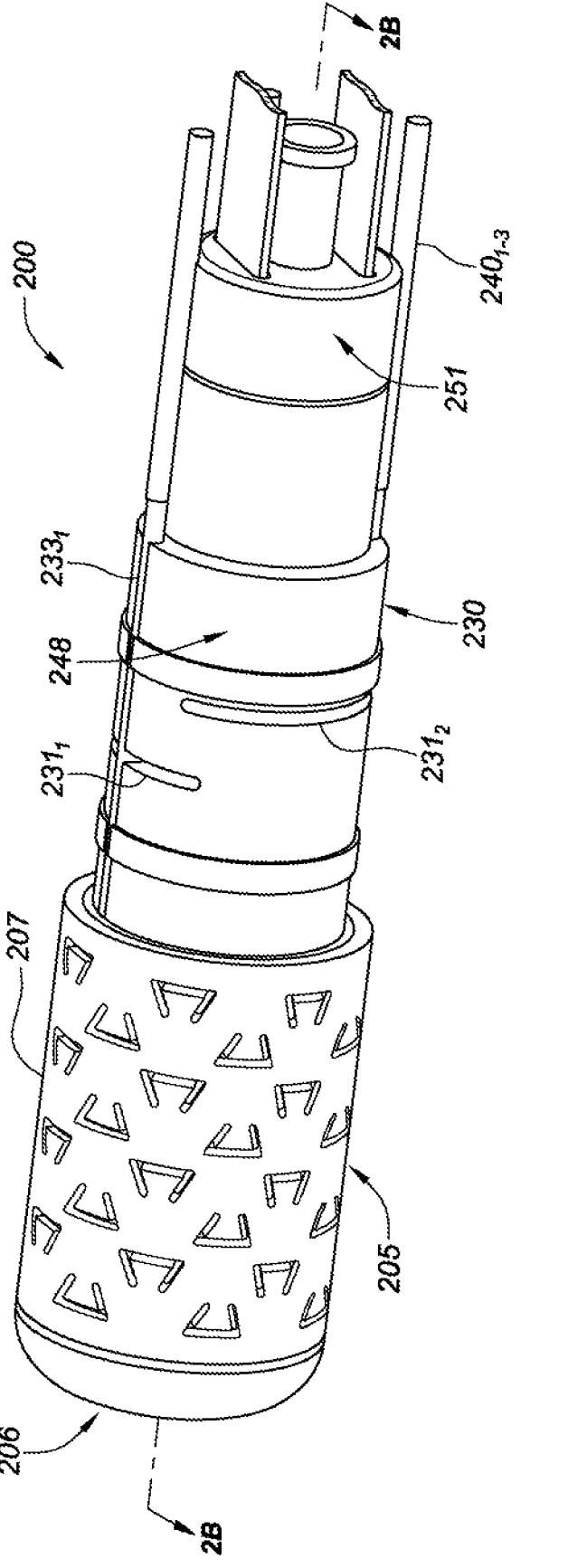
FIG. 2A is an isometric front view of an ablation catheter tip assembly, consistent with various aspects of the present disclosure.
Figure 2B:
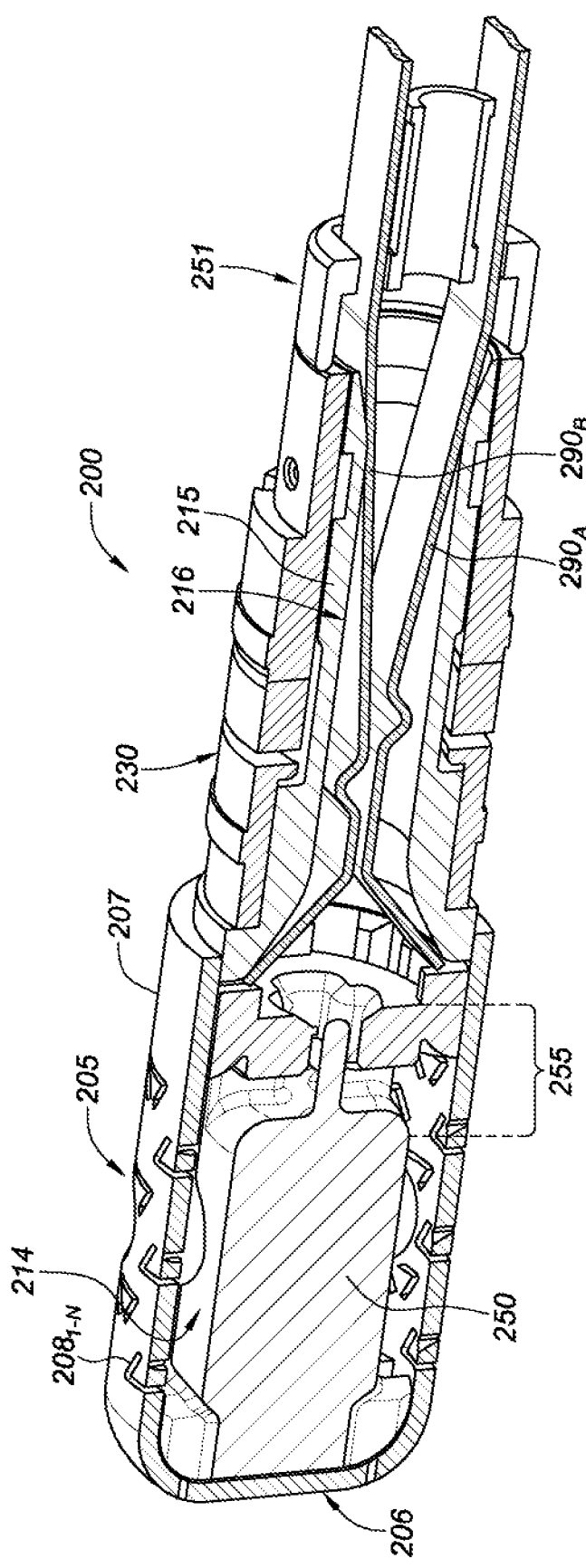
FIG. 2B is a cross-sectional, isometric front view of the ablation catheter tip assembly of FIG. 2A, consistent with various aspects of the present disclosure.
Figure 2C:
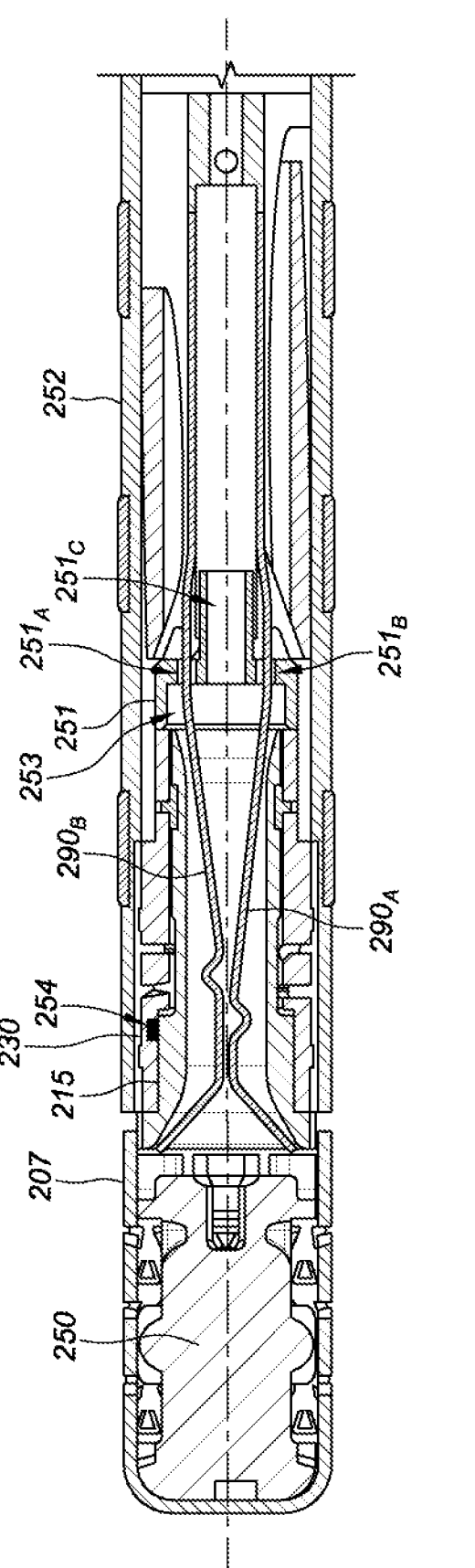
FIG. 2C is a cross-sectional front view of the ablation catheter tip assembly of FIG. 2A, with the ablation catheter tip assembly coupled to a distal end of a catheter shaft, consistent with various aspects of the present disclosure.

FIG. 2A is an isometric side view of a partial ablation catheter tip assembly 200, FIG. 2B is an isometric, cross-sectional side view of the partial ablation catheter tip assembly of FIG. 2A, and FIG. 2C is a cross-sectional side view of the partial ablation catheter tip assembly of FIG. 2A mounted to a distal end of a catheter shaft, consistent with various embodiments of the present disclosure.

Referring to FIGS. 2A-B, partial ablation catheter tip assembly 200 includes a tip 205 that is coupled to a distal end of a manifold 215. The manifold 215 may be comprised of, for example, a stainless steel alloy, MP35N (a cobalt chrome alloy), titanium alloy, or a composition thereof. The tip 205 includes a distal tip 206 and a member 207. The member 207 facilitates deformation of the tip in response to contact with tissue; more specifically, the member 207 deforms to increase surface contact with target tissue. The increased tissue surface contact improves outcomes for various diagnostics and therapies (e.g., tissue ablation). After contact with target tissue is complete, the member 207 returns to an un-deformed state. The distal tip 206 may be coupled to the member 207 via an adhesive, weld, etc. A manifold 215, and an irrigation lumen 216 therein, extends through the structural member 230, delivering irrigant from the irrigation lumen to a dispersion chamber 214 formed between the tip 205 and a tip insert 250.

In various embodiments of the present disclosure, to limit the deformation of a structural member 230, partial ablation catheter tip assembly 200 may transmit a portion of a force exerted on tip 205 through the manifold 215 (bypassing structural member 230). The manifold 215 transmits the force to a catheter shaft 252 that is coupled to a proximal end of the tip assembly 200 (as shown in FIG. 2C).

Various embodiments of the tip 205 (in the form of a conductive shell) are readily envisioned herein. For example, the tip may comprise platinum, a platinum iridium composition, or gold. The tip (which may weigh, for example, 0.027 g) may comprise one or more parts or components. As shown in FIG. 2A, the tip may comprise a hemispherical or nearly-hemispherical domed distal end 206 and a member 207 which is in the form of a cylindrical body. In one embodiment, the wall thickness of the tip is 0.002 inches, but alternative wall thicknesses may also be utilized. The tip may be formed or manufactured by, for example, forging, machining, drawing, spinning, or coining. Also, the tip could be constructed from molded ceramic that has, for example, sputtered platinum on its external surface. In another alternative embodiment, the tip could be constructed from conductive ceramic material.

Although a single-layer tip 205 constructed from a thin layer of gold, for example, may perform in an magnetic resonance (MR) environment without causing undesirable or unmanageable MR artifacts, a conductive shell comprising an outer layer of a paramagnetic material such as platinum or platinum iridium, for example, may benefit from a multilayer construction as discussed below. A multilayer conductive shell may have just a multilayer cylindrical body portion, just a multilayer domed distal end portion, or both a multilayer domed distal end portion and a multilayer cylindrical body. Again, however, it is not a requirement that the distal tip 206 and the cylindrical body 207 (also referred to as a member) must both be constructed with the same number of layers or with the same thickness of layers. Also, the walls of the tip 205 may, for example, be of a total thickness that is the same as, or nearly the same as, the thickness of the single-layer conductive shell described above. The tip may be formed or manufactured per, for example, the techniques already described herein.

Platinum iridium (a paramagnetic material) is commonly used for constructing catheter tips. Thus, various embodiments disclosed herein utilizing a thin conductive shell constructed entirely from platinum or platinum iridium (or some other paramagnetic material) may induce MR artifacts in an MR environment. Alternatively, for MR applications, the conductive tip may comprise a single layer constructed entirely from a diamagnetic material (e.g., a thin gold conductive shell) or a multilayer conductive shell including, for example, a platinum iridium outer layer and a diamagnetic material (e.g., gold or copper) inner layer. In such an embodiment, the paramagnetic outer layer and the diamagnetic inner layer minimize or entirely mitigate undesirable MR artifacts. Alternatively, the multilayer conductive shell may have an outer layer constructed from a diamagnetic material (such as bismuth or gold) and an inner layer constructed from a paramagnetic material (such as platinum or platinum iridium).

In yet another embodiment (not shown), a multilayer conductive shell of a tip 205 may comprise more than two layers. For example, the conductive shell may comprise three layers, including a very thin outer layer of a paramagnetic material, a thicker intermediate layer of a diamagnetic material, and an oversized inner layer of a non-precious metal (or plastic or other material) sized to ensure that the finished geometry of the overall ablation tip is of a desired size for effective tissue ablation. Materials that may be used for the inner layer of the tip 205 include, but are not limited to, the following: silicon (metalloid); germanium (metalloid); bismuth (post transition metal); silver; and gold. Silver and gold are examples of elemental diamagnetic materials that have one-tenth the magnetic permeability of paramagnetic materials like platinum. Thus, one example multilayer shell configuration could comprise a platinum outer layer (or skin) and an inner layer (or liner or core) of gold or silver with a thickness ratio (e.g., platinum-to-gold thickness ratio) of at least $\frac{1}{10}$ (i.e., the platinum layer being one-tenth as thick as the gold layer). In another example, a multilayer conductive shell configuration could comprise a platinum outer layer and a bismuth inner layer with a thickness ratio (e.g., platinum-to-bismuth thickness ratio) of at least $\frac{1}{2}$ (i.e., the platinum outer layer being one-half as thick as the bismuth inner layer) since bismuth has a permeability that is about one-half the permeability of platinum. The layers may also be constructed from alloys, which may be used, for example, when a pure element material might otherwise be disqualified from use in the construction of a catheter tip.

The cross-sectional side views of FIGS. 2B and 2C of the partial ablation catheter tip assembly 200 help to illustrate irrigant flow there through. The irrigant flows from an irrigant source through a catheter handle and into a central lumen of catheter shaft 252. The central lumen delivers the irrigant to a distal end of the catheter shaft. Upon arriving at the distal end of the catheter shaft, the irrigant transitions into an irrigant lumen 216 of manifold 215 via end cap 251. Upon arriving at a proximal end of member 207, a dispersion feature 255 distributes the irrigant circumferentially around tip insert 250 into a dispersion chamber 214 between the tip insert and the member 207. The positive pressure within the dispersion chamber directs the irrigant radially out of the tip 205 via irrigant apertures $208_{1\text{-}N}$.

The tip insert 250 may be constructed from, for example, plastic (such as PEEK, which is polyether ether ketone) thermally-insulative ceramic (or other material with similar insulative properties), or ULTEM. The ablation tip inserts described herein are preferably constructed from thermally-insulative material.

In some embodiments, a member 207 of tip 205 may comprise a titanium alloy (or other metal alloy with characteristics including a high tensile strength).

As shown in FIG. 2A, structural member 230 houses a plurality of fiber optic cables $240_{1\text{-}3}$ that extend through grooves, for example groove $233_1$. In the present embodiment, the structural member 230 is divided into a plurality of segments along a longitudinal axis. The segments are bridged by flexure portions $231_{1\text{-}2}$, each flexure portion defining a neutral axis. Each of the neutral axes constitute a location within the respective flexure portions where the stress is zero when subjected to a pure bending moment in any direction.

In a fiber optic distance measurement sensor, fiber optic cables $240_{1\text{-}3}$ may be disposed in grooves 233, respectively, such that the distal ends of the fiber optic cables terminate at the gaps of either flexure portion $231_{1\text{-}2}$. As shown in FIGS. 2A, and 2B, flexure portions $231_{1\text{-}2}$ define a semicircular segment that intercepts an inner diameter of structural member 230. The flexure portions $231_{1\text{-}2}$ may be formed by the various ways available to the artisan, such as but not limited to sawing, laser cutting or electro-discharge machining (EDM).

As discussed above, one or more fiber optic cables 240 are mechanically coupled to structural member 230 via grooves 233. In some embodiments, each of the fiber optics may be communicatively coupled to a Fabry-Perot strain sensor bridged across one of the flexure portions 231$_{1\text{-}2}$. The Fabry-Perot strain sensor includes transmitting and reflecting elements on either side of the gap defined by the flexure portion to create an interferometric gap. The Fabry-Perot sensor includes transmitting and receiving elements. A free end of the transmitting element may be faced with a semi-reflecting surface, and a free end of the reflecting element may be faced with a semi-reflecting surface.

In some embodiments, structural member 230 may comprise a composition including a stainless steel alloy (or other metal alloy with characteristics including a high tensile strength, e.g., titanium), or platinum iridium (e.g., in a $^9/_{10}$ ratio).

In partial ablation catheter tip assembly 200 of FIGS. 2A and 2B, a trans-axial compliance of structural member 230 is corrected by directing a portion of a force exerted on tip 205 through manifold 215. By re-directing a portion of the trans-axial load onto the manifold 215, the resulting trans-axial deformation of the structural member 230 is reduced. In various embodiments of the present disclosure, the manifold may exhibit high deformation in response to axial force and reduced deformation in response to trans-axial forces. As a result, the manifold 215 will minimally increase the stiffness of the catheter tip assembly 200 in response to an axial force, while greatly increasing the stiffness in response to a trans-axial force. In some embodiments, the catheter tip assembly 200 may be tuned to target a 1:1 lateral-to-axial compliance ratio; for example, a 500:1 lateral-to-axial compliance ratio or less (1500 nanometers lateral motion to 3 nanometers axial).

Further referring to FIGS. 2A-C, the structural member 230 may be coupled at a distal end to a distal end of manifold 215, and at a proximal end to both the manifold 215 and an end cap 251. In some embodiments, the end cap may be made of platinum, titanium alloy, stainless steel alloy, MP35N (a cobalt chrome alloy), or a combination thereof. Once the tip assembly 200 is complete, the structural member 230 may be further coupled at a proximal end to a catheter shaft 252 (as shown in FIG. 2C) that extends proximally to a catheter handle. The structural member 230 is designed in such a way as to receive forces exerted on the tip 205 of the catheter tip assembly 200 and to absorb such force by deflecting and deforming in response thereto. Further, and as discussed in more detail above, the structural member 230 may be outfitted with a measurement device which facilitates measurement of the deflection/deformation of the deformable body which may be correlated with the force exerted on the tip 205 and communicated with a clinician. Knowledge of a force exerted on the tip 205 of a catheter may be useful for a number of different cardiovascular operations; for example, during a myocardial tissue ablation therapy it is desirable to know a contact force exerted by the tip 205 of the catheter on target tissue as the time to necrose tissue is based on energy transferred between the catheter and tissue—which is highly dependent upon the extent of tissue contact.

In the various catheter tip assemblies disclosed herein, various electronic components in the catheter tip are necessary to facilitate desired functionality. As discussed in more detail above, the catheter tip may include, for example, one or more radio-frequency ablation electrodes, one or more electrophysiology electrodes, and/or a plurality of thermocouples. All of these electronic components must be communicatively coupled to a computer system at a proximal end of the catheter (as discussed above in reference to FIG. 1). Prior art ablation catheter systems utilized individual lead wires, extending the length of the catheter shaft, to facilitate communication between the various distal tip components and the computer system. Aspects of the present disclosure are directed to reduced catheter assembly complexity by using one or more flexible circuits which extend at least a portion of the length of the catheter shaft, and communicatively couple the electronic components to the computer system.

In the embodiment disclosed in FIGS. 2A-C, flexible circuits 290$_{A\text{-}B}$ are routed through an irrigant lumen 216 of manifold 215, the same cross-sectional path taken by irrigant delivered to the dispersion chamber 214. The irrigant fluid flow path traverses through end cap 251 (via irrigant aperture 251$_C$) into the start of the shared space with the flexible circuits, within the irrigant lumen 216. The irrigant then flows around the flexible circuits in the irrigant lumen and into the dispersion chamber 214, via a dispersion feature 255, before exiting through irrigant apertures 208$_{1\text{-}N}$.

As shown in FIG. 2C, flexible circuits 290$_{A\text{-}B}$ extend proximally through irrigant lumen 216 of manifold 215, through auxiliary apertures 251$_{A,B}$ in end cap 251, and into catheter shaft 252. The flexible circuits 290$_{A\text{-}B}$ may extend a length of the catheter shaft, or otherwise, may be communicatively coupled to another flexible circuit or a plurality of lead wires somewhere within the catheter shaft. In such embodiments, the flexible circuits 290$_{A\text{-}B}$ may include one or more connectors at proximal ends of the circuits which facilitate electrical coupling to another flexible circuit or lead wires.

While for illustrative purposes flexible circuits 290$_{A\text{-}B}$ are shown to end at tip insert 250, the flexible circuits 290$_{A\text{-}B}$ may extend into the dispersion chamber 214, between the flexible tip 205 and the tip insert 250, and circumferentially extend around at least a portion of the tip insert 250. In alternative embodiments, individual lead wires may extend from distal ends of the flexible circuits 290$_{A\text{-}B}$ and electrically couple the flexible circuits to electrical components within the tip 205 (e.g., thermocouples, microelectrodes, etc.).

In various embodiments, the flexible circuits 290$_{A\text{-}B}$ are integrated into a single flexible circuit in the tip region, and include a plurality of thermocouples which are placed into thermal contact with the tip 205 to conduct high-thermal sensitivity monitoring of an ablation therapy. The thermal sensors may be positioned in close proximity to, and preferably to be in physical contact with, an inner surface of the tip 205. As used herein, "in close proximity to" means, for example, within 0.0002 to 0.0010 inches, particularly if a conductive adhesive or other bonding technique is used to bond the temperature sensors to the inner surface of the tip. Depending on the specific properties of the sensors, the construction and materials used for the tip, and the type of conductive adhesive or the other bonding technique employed, it is possible that enough temperature sensitivity may be achieved despite even larger gaps between the sensors and the tip.

In yet further embodiments, the flexible circuit in the tip region includes one or more microelectrodes which facilitate electrophysiology monitoring of tissue in contact with the tip 205.

As shown in FIG. 2C, structural member 230 of partial ablation catheter tip assembly 200 is designed in such a way as to receive forces exerted on the tip 205 and to absorb such force by deflecting and deforming in response thereto. As the structural member 230 is coupled to manifold 215 at a distal end of the manifold 215, axial compression of the structural member 230 results in proximal movement of the manifold. To facilitate such axial motion of the manifold, end cap 251 includes a cavity 253 into which a proximal end of the manifold may extend into in response to an axial force on the catheter tip assembly 200. By facilitating axial motion of the manifold, the structural member 230 receives substantially all of an axial load exerted on the catheter tip, while only absorbing a portion of lateral loads exerted on the catheter tip. As discussed above, such a structural configuration facilitates a reduced lateral-to-axial compliance ratio of a sub-assembly 248 (FIG. 2A) of tip assembly 200, which is desirable for improved force measurement repeatability. Moreover, aspects of the present embodiment allow for increased axial movement, for example 4-5 nanometer/gram, while allowing the option to keep fiber optic movement in response to a lateral force to less than 1000 nanometers per 50 grams load.

As can be seen in FIG. 2C, a thermocouple 254 may be positioned between the structural member 230 and the manifold 215. The thermocouple 254 outputs a signal which is used by controller circuitry to compensate for temperature variation that may affect the output signals of the fiber optics 240 on the structural member 230. To facilitate placement of the thermocouple 254 at a distal end of the structural member, lead wires to the thermocouple may be routed within grooves 233 in the outer diameter of the structural member.

Figure 3:
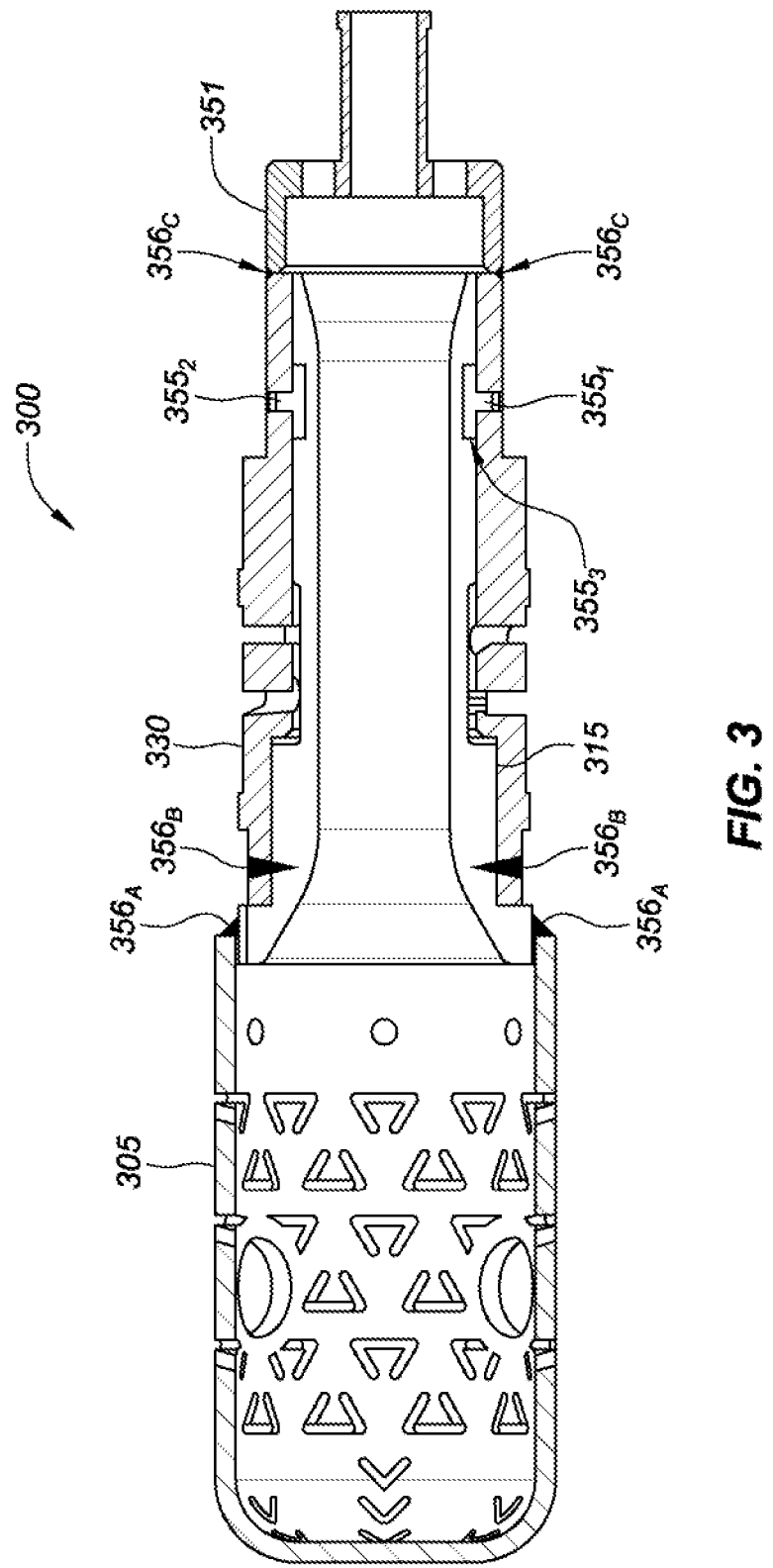
FIG. 3 is a cross-sectional, front view of a partial ablation catheter tip assembly, consistent with various aspects of the present disclosure.

FIG. 3 is a cross-sectional, front view of an ablation catheter tip assembly 300, consistent with various aspects of the present disclosure.

Manifold 315 is coupled to structural member 330 at a distal end via a (laser) weld $356_B$. A distal end of the manifold 315 is also coupled to tip 305 via a (laser) weld $356_A$. An end cap 351 is coupled to the structural member 330 via a (laser) weld $356_C$.

As shown in the present embodiment, the (laser) welds $356_{A-C}$ may be continuous welds which extend circumferentially about a longitudinal axis, or, alternatively, a number of spot welds may be placed about the circumference. However, it is desirable for at least the weld $356_C$ to be hermetically sealed to prevent irrigant from within the end cap 351 and manifold 315 from egressing into a space between the structural member 330 and catheter shaft, and thereby effecting force sensing.

Injection and vent holes $355_1$ extend through structural member 330, and match-up with a groove $355_3$ in manifold 315, which provides a space for silicone sealant $355_2$. The silicone sealant may range from 20 A through 90 A durometers, for example. The silicone sealant is injected to form a hermetic seal between the manifold and structural member, further preventing egress of irrigant into the space between the structural member 330 and catheter shaft.

It is to be understood that while an irrigated ablation catheter tip is illustrated in various embodiments of the present disclosure, the design of the structural assembly (including the structural member 330, manifold 315, and end cap 351) is modular and may facilitate the fitting of various catheter tips (e.g., rigid, flex, and other advanced irrigation tips).

In various embodiments of the catheter tip assemblies disclosed herein, the catheter tip assemblies may also include a plurality of spot electrodes on a conductive shell thereof which facilitate electrophysiology mapping of tissue, such as myocardial tissue, in (near) contact with the shell. In more specific embodiments, the plurality of spot electrodes may be placed across the shell in such a manner as to facilitate Orientation Independent Algorithms which enhance electrophysiology mapping of the target tissue and is further disclosed in U.S. application Ser. No. 15/152,496, filed 11 May 2016, U.S. application Ser. No. 14/782,134, filed 7 May 2014, U.S. application Ser. No. 15/118,524, filed 25 Feb. 2015, U.S. application Ser. No. 15/118,522, filed 25 Feb. 2015, and U.S. application Ser. No. 62/485,875, filed 14 Apr. 2017, all of which are now pending, and are incorporated by reference as though fully disclosed herein.

Applicant further envisions utilizing catheters comprising various segmented tip designs with the ablation catheter system described above. Example tip configurations are disclosed in U.S. patent application Ser. No. 61/896,304, filed 28 Oct. 2013, and in related international patent application no. PCT/US2014/062562, filed 28 Oct. 2014 and published 7 May 2015 in English as international publication no. WO 2015/065966 A2, both of which are hereby incorporated by reference as though fully set forth herein.

Although several embodiments have been described above with a certain degree of particularity, those skilled in the art could make numerous alterations to the disclosed embodiments without departing from the present disclosure. It is intended that all matter contained in the above description or shown in the accompanying drawings shall be interpreted as illustrative only and not limiting. Changes in detail or structure may be made without departing from the present teachings. The foregoing description and following claims are intended to cover all such modifications and variations.

Various embodiments are described herein of various apparatuses, systems, and methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," "an embodiment," or the like, means that a particular feature, structure, or characteristic described in connection with the embodiment is included in at least one embodiment. Thus, appearances of the phrases "in various embodiments," "in some embodiments," "in one embodiment," "in an embodiment," or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. An ablation catheter tip assembly comprising:
a tip comprising a conductive shell and a tip insert, the tip insert being thermally insulative, the tip defining a dispersion chamber between the conductive shell and the tip insert;
a metal structural member coupled to a proximal portion of the tip;
a metal manifold having a distal end welded to a distal portion of the metal structural member, an outer circumference of the metal manifold contacting an inner circumference of the metal structural member at a plurality of locations, the metal manifold defining an irrigation lumen extending through the metal manifold along a longitudinal axis thereof;
an annular dispersion feature disposed inside the conductive shell longitudinally between the distal end of the metal manifold and the dispersion chamber; and
a plurality of flexible electronic circuits that extend through the irrigation lumen of the metal manifold,
wherein the irrigation lumen terminates proximally adjacent to the annular dispersion feature such that irrigant is configured to be delivered from a distal end of the irrigation lumen, through the annular dispersion feature, and into the dispersion chamber, and
wherein the annular dispersion feature is configured to distribute the irrigant into the dispersion chamber and circumferentially around the tip insert between the tip insert and the conductive shell for dispersion through the conductive shell.

2. The ablation catheter tip assembly of claim 1, further including an end cap configured to facilitate axial motion of the metal manifold relative to the metal structural member, wherein a proximal portion of the metal structural member is welded to a distal portion of the end cap.

3. The ablation catheter tip assembly of claim 1,
wherein the conductive shell surrounds at least a portion of the tip insert, and
wherein the plurality of flexible electronic circuits are integrated into a single flexible electronic circuit in the tip, and wherein the single flexible electronic circuit is wrapped around the tip insert, and includes a plurality of thermal sensors that are in thermal communication with the conductive shell and are distributed across at least one of a length and width of the single flexible electronic circuit,
the ablation catheter tip assembly further comprising a communication pathway at least partially disposed on the single flexible electronic circuit, communicatively coupling the plurality of thermal sensors to a computer system.

4. The ablation catheter tip assembly of claim 3, wherein the single flexible electronic circuit further includes a plurality of electrical components that are positioned in electrical isolation from the conductive shell and are communicatively coupled to the computer system via the communication pathway.

5. The ablation catheter tip assembly of claim 1, wherein the metal structural member includes a plurality of holes, and the metal manifold includes a groove that aligns with the plurality of holes of the metal structural member,
the ablation catheter tip assembly further comprising a silicone sealant at least partially filling the groove of the metal manifold and the plurality of holes of the metal structural member, the silicone sealant configured to hermetically seal the irrigant flowing within the irrigation lumen of the metal manifold from an exterior of the metal structural member.

6. The ablation catheter tip assembly of claim 1, further including a thermocouple positioned between the metal structural member and the metal manifold, the thermocouple configured to output a signal indicative of temperature and to facilitate compensation of temperature variation induced error in a fiber optic measurement system on the metal structural member.

7. The ablation catheter tip assembly of claim 1, wherein the metal structural member is further configured to absorb a first portion of a lateral force exerted on the conductive shell, and the metal manifold is configured to absorb a second portion of the lateral force exerted on the conductive shell, wherein the lateral force is a component of an overall force exerted on the conductive shell, and wherein the metal manifold and the metal structural member, as combined, have a lateral-to-axial compliance ratio less than 500:1.

8. The ablation catheter tip assembly of claim 1, wherein a trans-axial compliance of the metal structural member is configured to be corrected by directing a portion of a force exerted on the conductive shell through the metal manifold.

9. The ablation catheter tip assembly of claim 2, wherein axial compression of the metal structural member results in proximal movement of the metal manifold through a cavity defined in the end cap.

10. The ablation catheter tip assembly of claim 6, wherein a second thermocouple is positioned to be in physical contact with an inner surface of the conductive shell.

11. The ablation catheter tip assembly of claim 6, wherein a second thermocouple is bonded within 0.0002 to 0.0010 inches of an inner surface of the conductive shell.

12. The ablation catheter tip assembly of claim 1, wherein lead wires to a thermocouple are routed within grooves in an outer diameter of the metal structural member.

13. The ablation catheter tip assembly of claim 6, wherein lead wires to the thermocouple are routed within grooves in an outer diameter of the metal structural member.

14. The ablation catheter tip assembly of claim 2, wherein the plurality of flexible electronic circuits extend into the irrigation lumen through the end cap.

* * * * *